(12) United States Patent
Zhang et al.

(10) Patent No.: US 10,849,822 B2
(45) Date of Patent: Dec. 1, 2020

(54) CONTROL METHOD AND CONTROL DEVICE FOR CESSATION OF VOMITING

(71) Applicant: WAT MEDICAL TECHNOLOGY INC., Ningbo (CN)

(72) Inventors: Jun Zhang, Ningbo (CN); Yun Xiang, Ningbo (CN); Lijuan Wang, Ningbo (CN); Yurong Xu, Ningbo (CN); Mingshan Sun, Ningbo (CN)

( * ) Notice: Subject to any disclaimer, the term of this patent is extended or adjusted under 35 U.S.C. 154(b) by 112 days.

(21) Appl. No.: 16/192,170

(22) Filed: Nov. 15, 2018

(65) Prior Publication Data

US 2019/0183727 A1    Jun. 20, 2019

Related U.S. Application Data

(63) Continuation of application No. PCT/CN2017/079708, filed on Apr. 7, 2017.

(30) Foreign Application Priority Data

May 16, 2016    (CN) .......................... 2016 1 0326410

(51) Int. Cl.
*A61H 39/00*    (2006.01)
*A61N 1/36*    (2006.01)
(Continued)

(52) U.S. Cl.
CPC ....... *A61H 39/002* (2013.01); *A61B 5/02438* (2013.01); *A61H 39/00* (2013.01);
(Continued)

(58) Field of Classification Search
CPC .................. A61H 39/002; A61H 39/00; A61H 2201/5043; A61H 2201/1207;
(Continued)

(56) References Cited

U.S. PATENT DOCUMENTS 7,489,973 B2    2/2009    Shan
8,050,776 B2    11/2011    Shan
(Continued)

FOREIGN PATENT DOCUMENTS

CN    2676947 Y    2/2005
CN    1689660 A    11/2005
(Continued)

OTHER PUBLICATIONS

Internation Search Report of PCT/CN2017/079708, dated Jun. 29, 2017.

*Primary Examiner* — Amanda K Hulbert
*Assistant Examiner* — Philip C Edwards
(74) *Attorney, Agent, or Firm* — W&K IP

(57) ABSTRACT

The disclosure discloses an antiemetic control device and a control method thereof, comprising a housing, a MCU single-chip microcontroller provided in the housing, a charging circuit, a discharging circuit and a rechargeable battery for supplying power, a button, a display screen, an alarm device and a plurality of mode indicator lights disposed on the housing, two electrodes and an optical pulse detecting unit disposed on the lower surface of the housing, and two wrist straps disposed on the housing. The disclosure has the characteristics of stable therapeutic effects.

8 Claims, 4 Drawing Sheets

(51) Int. Cl.
 *A61B 5/024* (2006.01)
 *A61B 5/00* (2006.01)
(52) U.S. Cl.
 CPC ............ *A61N 1/36* (2013.01); *A61B 5/02416* (2013.01); *A61B 5/681* (2013.01); *A61B 5/746* (2013.01); *A61H 2201/0153* (2013.01); *A61H 2201/0188* (2013.01); *A61H 2201/1207* (2013.01); *A61H 2201/165* (2013.01); *A61H 2201/5025* (2013.01); *A61H 2201/5043* (2013.01); *A61H 2201/5097* (2013.01)
(58) Field of Classification Search
 CPC ...... A61H 2201/5025; A61H 2201/165; A61B 5/02438; A61B 5/02416; A61B 5/681
 USPC ......................................................... 607/62
 See application file for complete search history.

(56) References Cited

U.S. PATENT DOCUMENTS

| | | | | |
|---|---|---|---|---|
| 2009/0149921 | A1* | 6/2009 | Shah | A61N 1/32 607/72 |
| 2013/0103119 | A1 | 4/2013 | Yamanaka et al. | |
| 2014/0135631 | A1* | 5/2014 | Brumback | A61B 5/11 600/479 |

FOREIGN PATENT DOCUMENTS

| | | |
|---|---|---|
| CN | 103055416 A | 4/2013 |
| CN | 104784818 A | 7/2015 |
| CN | 204890963 U | 12/2015 |

\* cited by examiner

CONTROL METHOD AND CONTROL DEVICE FOR CESSATION OF VOMITING

CROSS-REFERENCE TO RELATED APPLICATIONS

This application is a continuation of International Patent Application No. PCT/CN2017/079708 with a filing date of Apr. 7, 2017, designating the United States, now pending, and further claims priority to Chinese Patent Application No. 201610326410.4 with a filing date of May 16, 2016. The content of the aforementioned applications, including any intervening amendments thereto, are incorporated herein by reference.

TECHNICAL FIELD

The disclosure relates to the technical field of medical instruments, in particular to an antiemetic control device and a control method with stable curative effect.

BACKGROUND

The mechanism of vomiting caused by chemotherapy drugs is very complicated and is not fully understood. Some scholars believe that the whole process is mainly controlled by the vomiting center. It is generally believed that the vomiting center is located in the small cell cytoplasmic structure of the brainstem, which on one hand receives stimulation from the throat, the gastrointestinal tract, the mediastinum and the high-grade cortical center, and on the other hand receives stimulation from the chemical sensory excitation zone. Both pathways can stimulate the center to cause vomiting reflexes.

Antiemetic drugs are usually used to block the conduction pathways of various neurotransmitters. However, antiemetic drugs generally cause problems such as constipation, lethargy, dry mouth, blurred vision and other adverse reactions. Besides the patient will develop drug resistance, and the drug's efficacy will decrease as the drug is used for a prolonged period of time.

Commonly used antiemetic control devices have deficiencies that the therapeutic effects for the patient decline as the usage time is prolonged.

Chinese patent publication No. CN204890963U with a publication date of Dec. 23, 2015 discloses an electronic antiemetic device comprising an upper cover and a lower cover. A circuit board is disposed between the upper cover and the lower cover. The upper cover comprises a screen and a control panel. The back of the lower cover is provided with a pair of pulse pieces, and the control panel is provided with a touch button. The insufficiency of this disclosure is that the therapeutic effects for the patient decline as the usage time is prolonged.

SUMMARY

The object of the present disclosure is to overcome the insufficiency of the antiemetic device in the prior art, which causes the therapeutic effects for the patient decline as the usage time is prolonged, and provides a antiemetic control device and a control method with stable therapeutic effects.

In order to achieve the above object, the present disclosure adopts the following technical solutions:
An antiemetic control device comprises a housing a MCU microcontroller provided in the housing, a charging circuit, a discharging circuit and a rechargeable battery for power supply, a button, a display screen, an alarm and a plurality of mode indicator lights disposed on the housing, two electrodes and an optical pulse detecting unit disposed on the lower surface of the housing, and two wrist straps disposed on the housing. The optical pulse detecting unit includes a highly translucent cover connected to the lower surface of the housing, an LED lamp disposed within the highly translucent cover for emitting detection light to the skin surface and a photodetector for receiving reflected light. The MCU microcontroller is electrically connected to the charging circuit, the discharging circuit, the display screen, the button, the LED lamp, the alarm, the photodetector and the plurality of mode indicator lights, respectively, and the rechargeable battery, the charging circuit, the discharging circuit and the two electrodes are electrically connected in sequence.

The disclosure simulates the bioelectrophysiological signal and periodically releases weak electricity to generate electrical stimulation. The excited electrical signal generated by the electrical stimulation passes through the nerve to the forecourt center and senses the stimulation signal, counteracting or weakening the excessive bioelectricity generated by the vestibule due to excessive movement of the human body. The transmission of vestibular nerve impulses to the center are reduced or suppressed, thereby increasing the tolerance of the vestibular organs to various motor stimuli and causing the gastric motility to return to normal. The nausea and vomiting will stop after the gastric motility is normal, and provides a favorable effect of preventing vomiting.

The display is used to display mode information and power information. The user can shift modes according to the mode information and replace the rechargeable battery according to the power information.

The MCU microcontroller controls the charging circuit to pre-charge the storage capacitor by using the energy of the rechargeable battery, and the output energy intensity is determined by the capacitor charging voltage.

The MCU microcontroller controls the energy input discharging circuit kept in the charging circuit, and the MCU microcontroller controls the discharging circuit to output positive and negative alternating pulses through the two electrodes.

After the control device is powered on, it is always in the standby state. When the button is held down for a long time, the MCU microcontroller is started, and the button is pressed to adjust the output intensity. Each time the button is pressed, the mode is increased by one in a cycle. The two electrodes are located near the Neiguan point on the wrist. As the mode increases, the pulse amplitude of the output of the discharging circuit gradually increases, and the stimulation of the Neiguan point on the wrist by the electric shock is stronger. After button is held down or the control device has operated for a period of time, the MCU microcontroller controls the two electrodes to stop operation through the discharging circuit.

Preferably, both electrodes are oblong and arranged in parallel on the lower surface of the housing, and the two electrodes are connected by an insulating link. The insulating link is connected to a rotating motor provided in the housing through a connecting column, and the rotating motor is electrically connected with the MCU microcontroller. The two electrodes can provide electric pulse stimulation around the Neiguan point and the stimulation effect is improved. The human body would be less likely to adapt, and the human body's response to the electric pulse stimulation would not decline.

Preferably, the control device further comprises a memory and a wireless transceiver disposed in the housing. The memory and the wireless transceiver are electrically connected to the MCU microcontroller. The wireless transceiver sends the date, the start time and the stop time of each process of the electrical pulse stimulation to a hospital's information platform or a doctor's cellphone such that the doctor could adjust the treatment plan according to the patient's response Preferably, a plurality of protrusions are provided on both electrodes. Each protrusion can press the skin and randomly serve as a discharge point, and the skin randomly connects several pairs of corresponding protrusions of the two electrodes, thereby improving the uncertainty of the discharge path, reducing the adaptability of the human body, and improving the stability of the therapeutic effect.

Preferably, the control device further comprises a ring indicator light disposed outside the button, and the ring indicator light is electrically connected to the MCU microcontroller. Each time the button is pressed, the ring indicator lights up to let the user know if the button is pressed correctly.

A control method for the antiemetic control device comprises the following steps: The number of mode indicator lights is 5. The 5 mode indicator lights respectively correspond to modes 1 to 5. The number of pulses per unit time of a P_BUCK pulse signal corresponding to modes 1 to 5 is sequentially increased. The mode number is set to i. The initial value of i is 1.

(6-1) The display screen displays mode information and power information. The housing is fixed to a wrist of a user by the wrist straps so that the two electrodes are located on two sides of the Neiguan point. The button is held down to start the MCU microcontroller.

(6-2) The MCU microcontroller outputs a P_BUCK pulse signal corresponding to the mode i to the charging circuit.

(6-3) Each charging capacitor of the charging circuit is precharged by using the electric energy of the rechargeable battery. The MCU microcontroller outputs PWM_N and PWM_P signals to the discharging circuit. The two electrodes output positive and negative alternating sharp waveforms of mode i. The sharp waveform includes a strong sharp waveform with a frequency of A. A weak sharp waveform with a frequency B is arranged between adjacent pulses of the strong sharp waveform.

B is a random number greater than A.

(6-4) When i<5, each time the user presses the button, the value of i is increased by 1 and then proceeds to step (6-2). When i≥5, the value of i is firstly reduced by 5, and each time the user presses the button, the value of i is increased by 1 and then proceeds to step (6-2).

(6-5) During the electrical pulse stimulation of steps (6-2) to (6-4), the LED lamp emits light to the wrist, the photodetector receives the reflected light signal from the skin, and the MCU microcontroller calculates the pulse of the human body according to the reflected light signal of the skin.

(6-5-1) The display screen displays the pulse of the human body. If the pulse of the human body gradually grows larger as the electrical pulse stimulation continues, the MCU microcontroller controls the alarm to sound an alarm and proceeds to step (6-6).

(6-5-2) If the current mode number is greater than mode 1, and the pulse of the human body gradually grows smaller and stabilizes as the electrical pulse stimulation continues, the MCU microcontroller reduces the value of i by 1 and proceeds to step (6-2).

(6-6) After the user holds down the button or the MCU microcontroller operates for 20 to 30 minutes, the MCU microcontroller stops outputting the P_BUCK pulse signal, the PWM_N and PWM_P signals, and the two electrodes stop operation.

Preferably, both electrodes are oblong and arranged in parallel on the lower surface of the housing, and the two electrodes are connected by an insulating link. The insulating link is connected to a rotating motor provided in the housing through a connecting column, and the rotating motor is electrically connected with the MCU microcontroller. During the electrical pulse stimulation of steps (6-2) to (6-4), the following steps are further included: (7-1) The rotating motor controls the connecting column to drive the two electrodes to rotate clockwise by C degrees for each time interval T where C is a factor of 180. (7-2) The rotating motor controls the connecting column to drive the two electrodes to rotate counterclockwise by C degrees for each time interval T after a continuous clockwise rotation of 180 degrees, and proceeds to step (7-1) after a continuous counterclockwise rotation of 180 degrees.

Preferably, the control device further comprises a memory and a wireless transceiver disposed in the housing. The memory and the wireless transceiver are electrically connected to the MCU microcontroller, and the following steps are included: The MCU microcontroller stores a date, a start time and a stop time of the user's electrical pulse stimulation in the memory. The wireless transceiver sends the date, the start time and the stop time of each process of the electrical pulse stimulation to a hospital's information platform or a doctor's cellphone Preferably, A is 0.5 Hz to 3 Hz, and B is 20 Hz to 35 Hz.

Therefore, the disclosure has the following beneficial effects: A plurality of modes can be selected. The operation is convenient. The curative effect is stable.

Figure 1:
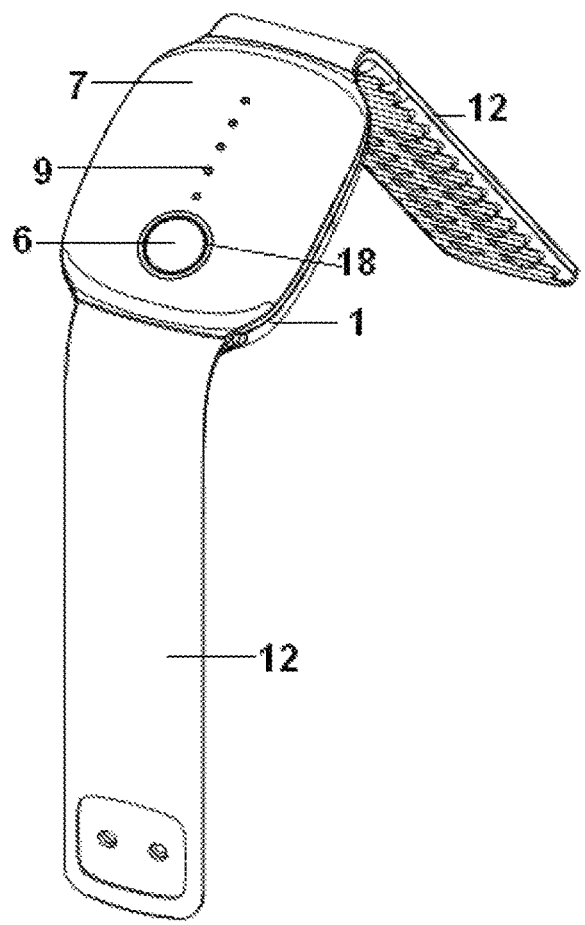
FIG. 1 is a schematic view showing the structure of the present disclosure.

Reference Numbers: housing 1, MCU microcontroller 2, charging circuit 3, discharging circuit 4, rechargeable battery 5, button 6, display screen 7, alarm 8, mode indicator light 9, electrode 10, optical pulse detecting unit 11, two wrist straps 12, highly translucent cover 111, LED lamp 112, photodetector 113, the insulated link 13, rotating motor 14, wireless transceiver 15, memory 16, protrusion 17, ring indicator light 18.

DETAILED DESCRIPTION

Embodiments of the present disclosure would be described in greater detail hereinafter in combination with the accompanying description and drawings.

Embodiment 1

Figure 2:
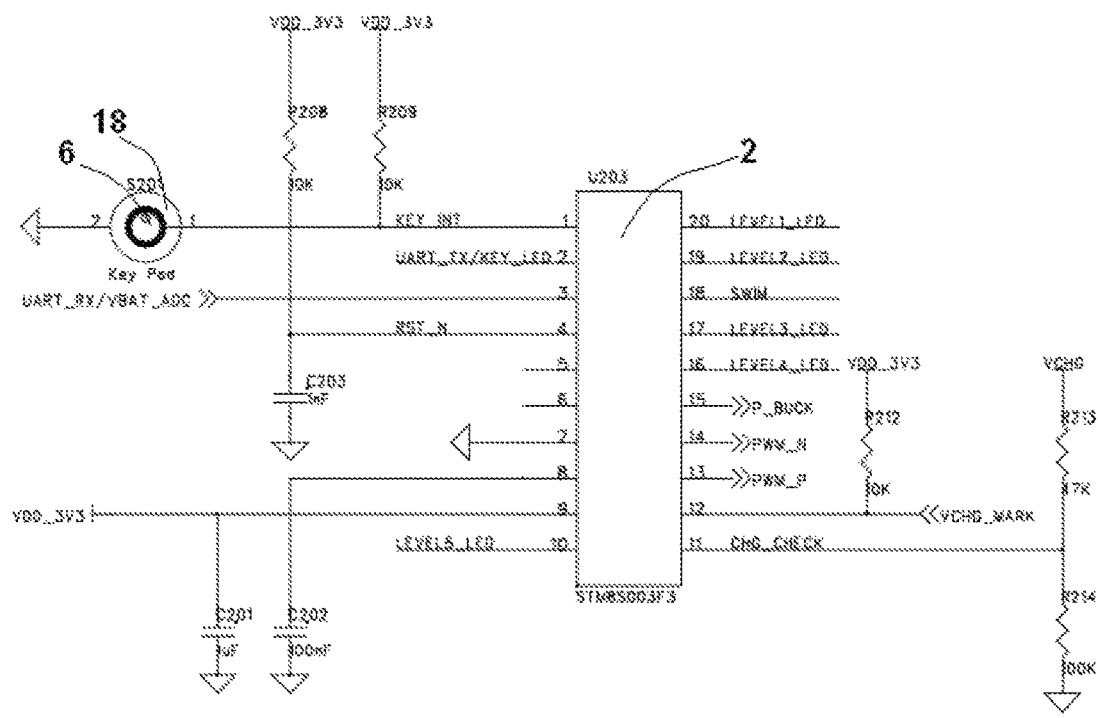
FIG. 2 is a circuit diagram of an MCU microcontroller of the present disclosure.
Figure 4:
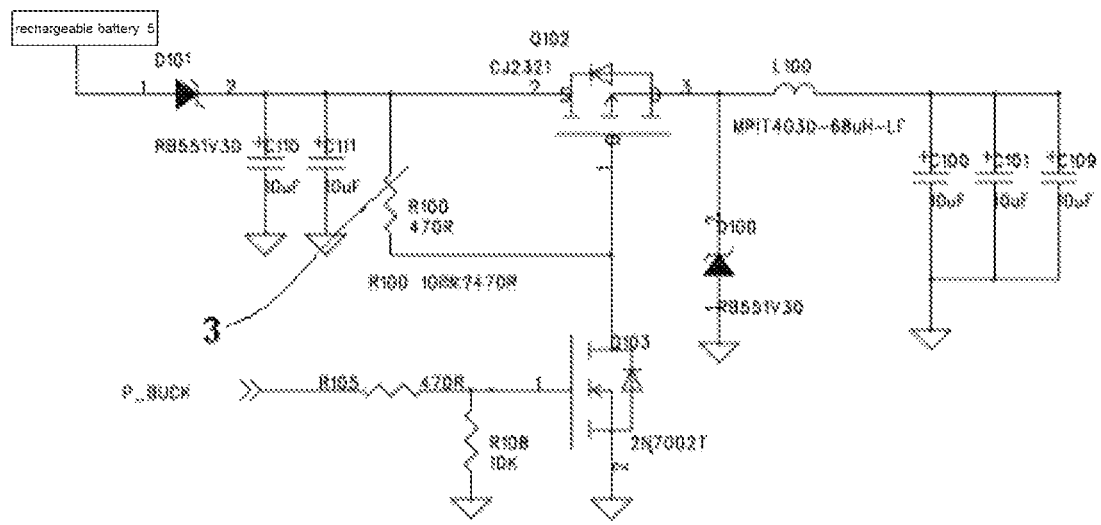
FIG. 4 is a circuit diagram of a charging circuit of the present disclosure.

The embodiment shown in FIG. 1, FIG. 2, and FIG. 4 is an antiemetic control device, comprising a housing 1, an MCU microcontroller 2, a charging circuit 3, a discharging circuit 4, and a rechargeable battery 5 for power supply.

Figure 3:
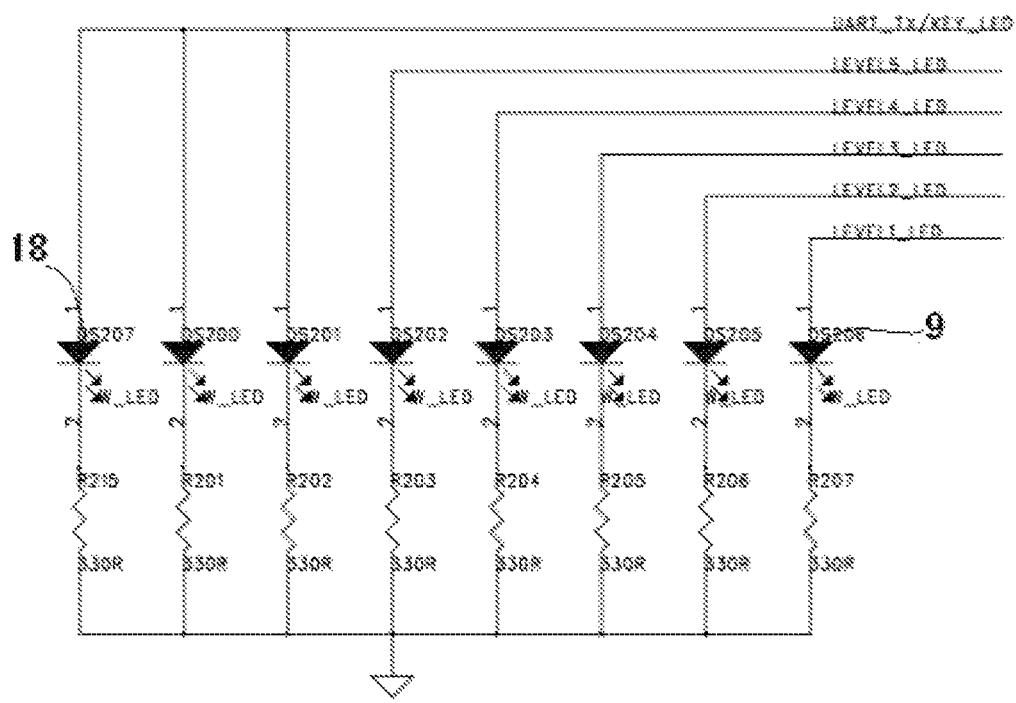
FIG. 3 is a circuit diagram of the mode indicator light and the ring indicator light of the present disclosure.
Figure 6:
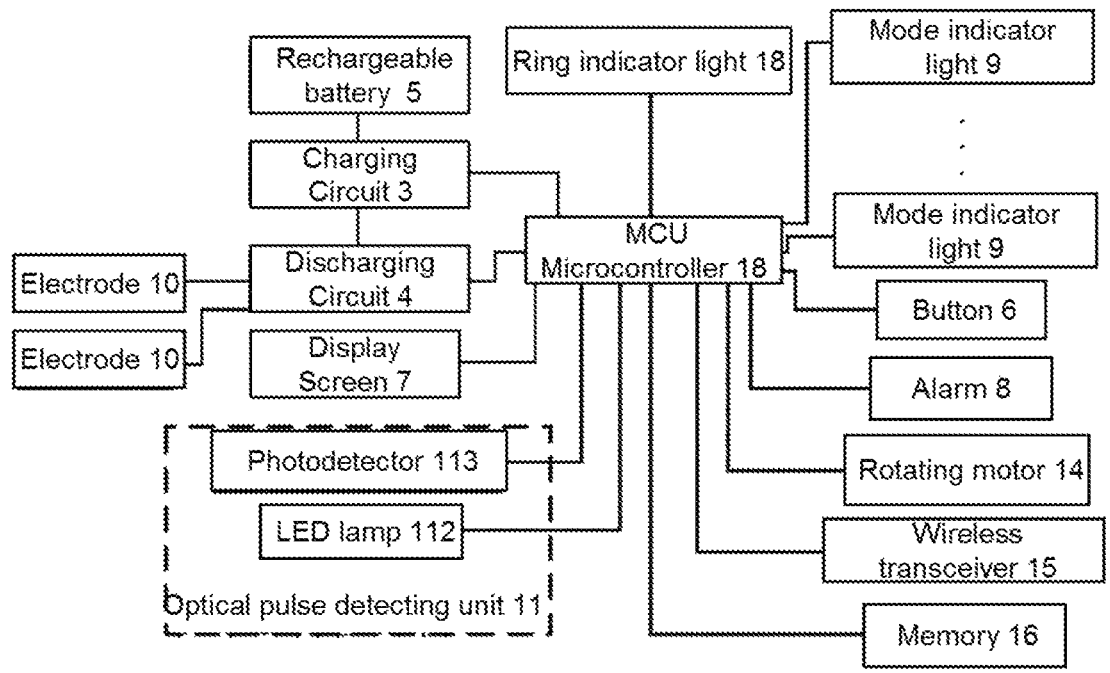
FIG. 6 is a schematic block diagram of the present disclosure.
Figure 8:
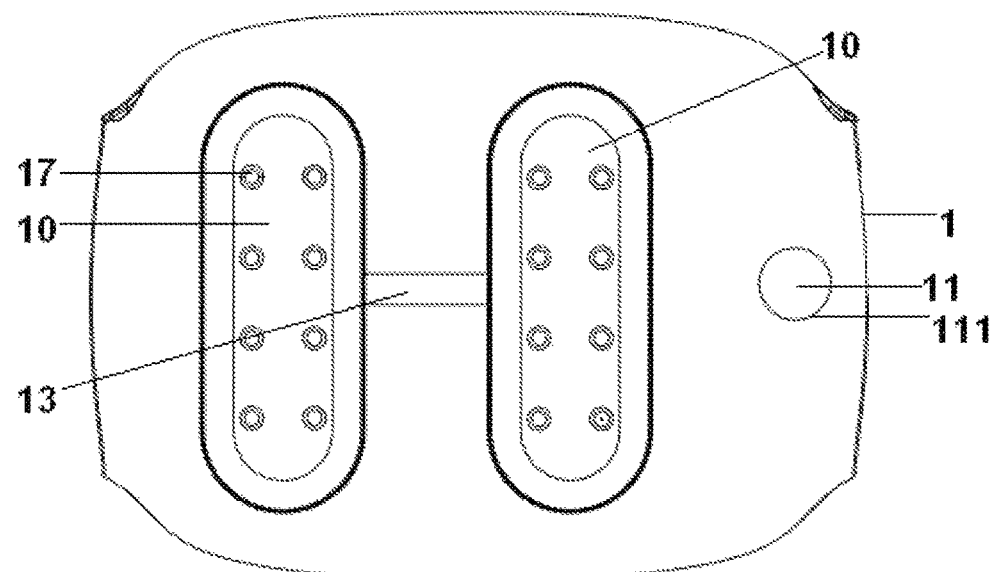
FIG. 8 is a schematic view showing the structure of the lower surface of the housing of the present disclosure.

FIG. 1, FIG. 3 and FIG. 6 show the button 6, the display screen 7, the alarm 8 and the five mode indicator lights 9. FIG. 8 shows the two electrodes 10 and an optical pulse detecting unit 11 disposed on the lower surface of the housing. As shown in FIG. 1, two wrist straps 12 are provided on the housing. As shown in FIG. 8, the optical pulse detecting unit includes a highly translucent cover 111 connected to the lower surface of the housing. As shown in FIG. 6, an LED lamp for emitting the detection light to the surface of the skin and a photodetector 113 for receiving the reflected light are disposed inside the highly translucent cover. The MCU microcontroller is electrically connected to the charging circuit, the discharging circuit, the display screen, the button, the LED lamp, the alarm, the photodetector and the plurality of mode indicator lights, respectively, and the rechargeable battery, the charging circuit, the discharging circuit and the two electrodes are electrically connected in sequence. Each of the two electrodes shown in FIG. 8 is provided with eight protrusions 17. As shown in FIG. 1, a ring indicator light 18 disposed outside the button is further included, and the ring indicator light is electrically connected to the MCIJ microcontroller.

As shown in FIG. 4, the charging circuit includes a diode D101, a diode D102, a capacitor C110, a capacitor C111, a capacitor C100, a capacitor C101 and a capacitor C109, a resistor R100, a resistor R105, a resistor R108, an inductor L100, a switch Q102, a switch Q103. The positive electrode of the diode D101 is connected to the rechargeable battery. The capacitor C110, the capacitor C111, the resistor R100 and the second pin of the switch Q102 are electrically connected to the negative electrode of the diode D101. The other ends of the capacitor C110 and the capacitor C111 are grounded, and the other end of the resistor R100 is respectively connected to the first pin of the switch Q102 and the third pin of the switch Q102. The second pin of the switch Q103 is grounded, and the first pin of the switch Q103 is electrically connected to one end of the resistor R105 and the resistor R108, respectively.

The other end of the resistor R108 is grounded, and the other end of the resistor R105 is electrically connected to the MCU microcontroller. The third pin of the switch Q102 is electrically connected to one end of the diode D100 and the inductor L100. The other end of the inductor L100 is respectively connected electrically with the capacitor C100, the capacitor C101, the capacitor C109, and the input end of the discharge circuit and the other ends of the capacitor C100, the capacitor C101, and the capacitor C109 are grounded.

Figure 5:
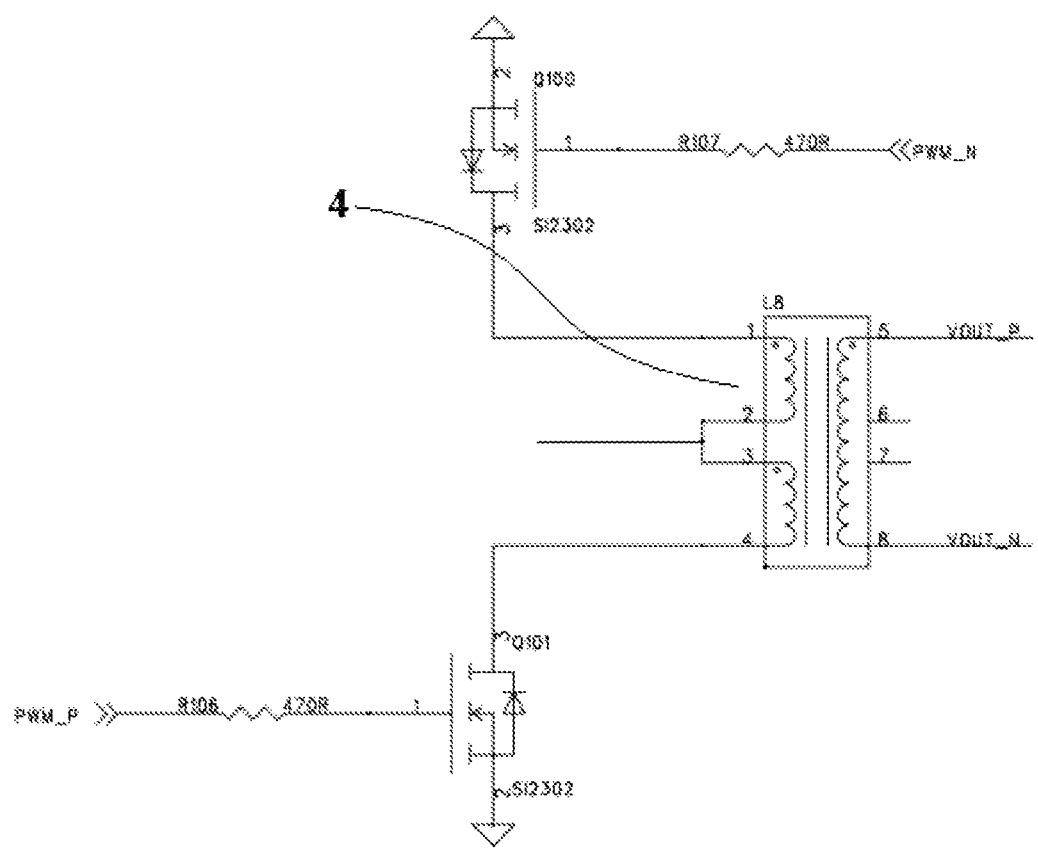
FIG. 5 is a circuit diagram of a discharging circuit of the present disclosure.

As shown in FIG. 5, the discharging circuit includes a transformer L8, a switch Q100, a switch Q101, a resistor R106, and a resistor R107. The first pin of the switch Q101 is electrically connected to the MCU microcontroller through the resistor R106. The first pin of the switch Q100 is electrically connected to the MCU microcontroller through the resistor R107. The second pins of the switch Q100 and the switch Q101 are grounded. The third pins of the switch Q100 and the switch Q101 are electrically connected with transformer L8. The transformer L8 is electrically connected with the charging circuit. VOUT_P and VOUT_N in the figure are connected to the two electrodes separately.

The amplitude of the pulse outputted by the two electrodes gradually increases with the increase of the mode. The amplitude of the output pulse of the first mode gradually increases from 10VP-P to 60VP-P. The amplitude of the output pulse of the fifth mode gradually increases from 10VP-P to 350VP-P. The maximum amplitude of the first mode is 60VP-P. The maximum amplitude of the second mode is 100VP-P. The maximum amplitude of the third mode is 160VP-P. The maximum amplitude of the fourth mode is 240VP-P, and the maximum amplitude of the fifth mode is 350VP-P. In each electric pulse stimulation process, and the pulse amplitude of the corresponding electrode output is increased once each time the pulses of PWM_N and PWM_P signals are output.

Figure 7:
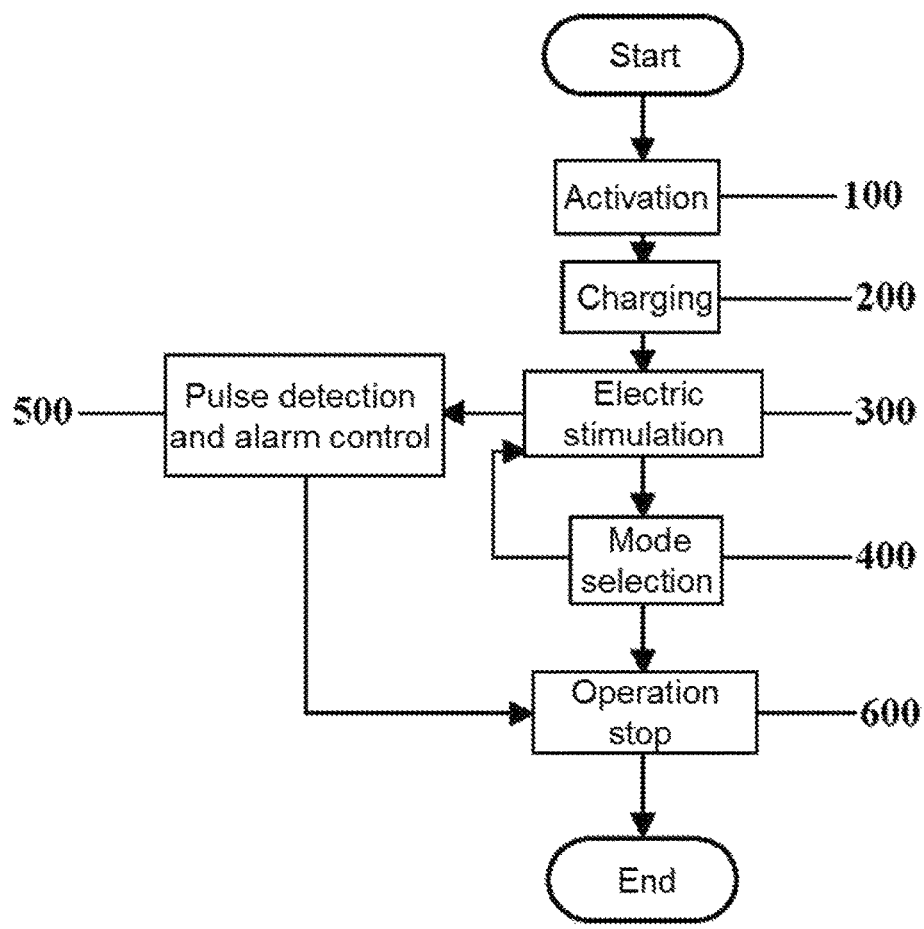
FIG. 7 is a flow chart of the first embodiment of the present disclosure.

A control method for the antiemetic control device as shown in FIG. 7 comprises the following steps: The number of mode indicator lights is 5. The 5 mode indicator lights respectively correspond to modes 1 to 5. The number of pulses per unit time of a P_BUCK pulse signal corresponding to modes 1 to 5 is sequentially increased. The mode number is set to i. The initial value of i is 1. The display screen displays mode information and power information. The housing is fixed to a wrist of a user by the wrist straps so that the two electrodes are located on two sides of the Neiguan point.

Step 100: Activation

The housing is fixed to a wrist of a user by the wrist straps so that the two electrodes are located on two sides of the Neiguan point. The display screen displays mode information and power information. The button is held down to start the MCU microcontroller.

Step 200: Charging

The MCU microcontroller outputs a P_BUCK pulse signal corresponding to the mode i to the charging circuit.

Step 300: Electric Stimulation

Each charging capacitor of the charging circuit is precharged by using the electric energy of the rechargeable battery. The MCU microcontroller outputs the PWM_N and PWM_P signals to the discharging circuit. The two electrodes output positive and negative alternating sharp waveforms of mode i. The sharp waveform includes a strong sharp waveform with a frequency of A. A weak sharp waveform with a frequency B is arranged between adjacent pulses of the strong sharp waveform. B is a random number greater than A. Both PWM_N and PWM_P are sharp waveforms. The sharp waveform includes a strong sharp waveform with a frequency of A. A weak sharp waveform with a frequency B is arranged between adjacent pulses of the strong sharp waveform. B is a random number greater than A.

Step 400: Mode Selection

When i<5, each time the user presses the button, the value of i is increased by 1 and then proceeds to step 200. When i≥5, the value of i is firstly reduced by 5, and each time the user presses the button, the value of i is increased by 1 and then proceeds to step 200.

Step 500: Pulse Detection and Alarm Control

During the electrical pulse stimulation of steps 200 to 400, the LED lamp emits light to the wrist, the photodetector receives the reflected light signal from the skin, and the MCU microcontroller calculates the pulse of the human body according to the reflected light signal of the skin.

Step 510: The display screen displays the pulse of the human body. If the pulse of the human body gradually grows larger as the electrical pulse stimulation continues, the MCU microcontroller controls the alarm to sound an alarm and proceeds to step 600.

Step 520: If the current mode number is greater than mode 1, and the pulse of the human body gradually grows smaller and stabilizes as the electrical pulse stimulation continues, the MCU microcontroller reduces the value of i by 1 and proceeds to step 200.

Step 600: Operation Stop

After the user holds down the button or the MCU microcontroller operates for 20 to 30 minutes, the MCU microcontroller stops outputting the P_BUCK pulse signal, the PWM_N and PWM_P signals, and the two electrodes stop operation. A is 1 Hz and B is 20 Hz to 35 Hz.

Embodiment 2

Embodiment 2 comprises all the structures and steps of embodiment 1. As shown in FIG. 8, both electrodes of embodiment 2 are oblong and arranged in parallel on the lower surface of the housing, and the two electrodes are connected by an insulating link 13. The insulating link is connected to a rotating motor 14 provided in the housing as shown in FIG. 6 through a connecting column, and the rotating motor is electrically connected with the MCU microcontroller. During the electrical pulse stimulation of steps 200 to 400 in embodiment 1, the following steps are further included: (7-1) The rotating motor controls the connecting column to drive the two electrodes to rotate clockwise by 5 degrees for each 20 seconds. (7-2) The rotating motor controls the connecting column to drive the two electrodes to rotate counterclockwise by 5 degrees for each 10 seconds after a continuous clockwise rotation of 180 degrees, and proceeds to step (7-1) after a continuous counterclockwise rotation of 180 degrees.

Embodiment 3

Embodiment 2 comprises all the structures and steps of embodiment 1 as well as a memory 16 and a wireless transceiver 15 disposed in the housing. The memory 16 and the wireless transceiver are electrically connected to the MCU microcontroller. Embodiment 3 further comprises the following steps: the MCU microcontroller stores a date, a start time and a stop time of the user's electrical pulse stimulation in the memory. The wireless transceiver sends the date, the start time and the stop time of each process of the electrical pulse stimulation to a hospital's information platform or a doctor's cellphone It is to be understood that the present invention is not intended to limit the scope of the invention. In addition, it is to be understood that various modifications and changes may be made to the present invention, and the equivalents of the scope of the invention.

The invention claimed is:

1. An antiemetic control device, comprising: a housing (1), a MCU microcontroller (2) provided in the housing, a charging circuit (3), a discharging circuit (4) and a rechargeable battery (5) for power supply, a button (6), a display screen (7), an alarm (8) and a plurality of mode indicator lights (9) disposed on the housing, two electrodes (10) and an optical pulse detecting unit (11) disposed on the lower surface of the housing, two wrist straps (12) disposed on the housing;

the optical pulse detecting unit includes a highly translucent cover (111) connected to the lower surface of the housing, an LED lamp (112) disposed within the highly translucent cover for emitting detection light to the skin surface and a photodetector (113) for receiving reflected light;

the MCU microcontroller is electrically connected to the charging circuit, the discharging circuit, the display screen, the button, the LED lamp, the alarm, the photodetector and the plurality of mode indicator lights, respectively, and the rechargeable battery, the charging circuit, the discharging circuit and the two electrodes are electrically connected in sequence;

wherein both electrodes are oblong and arranged in parallel on the lower surface of the housing, and the two electrodes are connected by an insulating link (13), the insulating link is connected to a rotating motor (14) provided in the housing through a connecting column, and the rotating motor is electrically connected with the MCU microcontroller.

2. The antiemetic control device according to claim 1, further comprising a memory and a wireless transceiver (15) disposed in the housing, the memory (16) and the wireless transceiver being electrically connected to the MCU microcontroller.

3. The antiemetic control device according to claim 1, wherein the two electrodes are provided with a plurality of protrusions (17).

4. The antiemetic control device according to claim 1, further comprising a ring indicator light (18) disposed outside the button, the ring indicator light being electrically connected to the MCU microcontroller.

5. A control method for the antiemetic control device according to claim 1, comprising the following steps:

the number of mode indicator lights is 5;

the 5 mode indicator lights respectively correspond to modes 1 to 5;

the number of pulses per unit time of a P_BUCK pulse signal corresponding to modes 1 to 5 is sequentially increased;

the mode number is set to i;

the initial value of i is 1;

(6-1) the display screen displays mode information and power information;

the housing is fixed to a wrist of a user by the wrist straps so that the two electrodes are located on two sides of the Neiguan point;

the button is held down to start the MCU microcontroller;

(6-2) the MCU microcontroller outputs a P_BUCK pulse signal corresponding to the mode i to the charging circuit;

(6-3) each charging capacitor of the charging circuit is precharged by using the electric energy of the rechargeable battery;

the MCU microcontroller outputs PWM_N and PWM_P signals to the discharging circuit;

the two electrodes output positive and negative alternating sharp waveforms of mode i;

the sharp waveform includes a strong sharp waveform with a frequency of A;

a weak sharp waveform with a frequency B is arranged between adjacent pulses of the strong sharp waveform;

B is a random number greater than A;

(6-4) when i<5, each time the user presses the button, the value of i is increased by 1 and then proceeds to step (6-2);

when i≥5, the value of i is firstly reduced by 5, and each time the user presses the button, the value of i is increased by 1 and then proceeds to step (6-2);

(6-5) during the electrical pulse stimulation of steps (6-2) to (6-4), the LED lamp emits light to the wrist, the photodetector receives the reflected light signal from the skin, and the MCU microcontroller calculates the pulse of the human body according to the reflected light signal of the skin;

(6-5-1) the display screen displays the pulse of the human body;

if the pulse of the human body gradually grows larger as the electrical pulse stimulation continues, the MCU microcontroller controls the alarm to sound an alarm and proceeds to step (6-6);

(6-5-2) if the current mode number is greater than mode 1, and the pulse of the human body gradually grows smaller and stabilizes as the electrical pulse stimulation continues, the MCU microcontroller reduces the value of i by 1 and proceeds to step (6-2);

(6-6) after the user holds down the button or the MCU microcontroller operates for 20 to 30 minutes, the MCU microcontroller stops outputting the P_BUCK pulse signal, the PWM_N and PWM_P signals, and the two electrodes stop operation.

6. The control method of the antiemetic control device according to claim 5, wherein both electrodes are oblong and arranged in parallel on the lower surface of the housing, and the two electrodes are connected by an insulating link, the insulating link is connected to a rotating motor provided in the housing through a connecting column, and the rotating motor is electrically connected with the MCU microcontroller;

and wherein during the electrical pulse stimulation of steps (6-2) to (6-4), the following steps are further included: (7-1) the rotating motor controls the connecting column to drive the two electrodes to rotate clockwise by C degrees for each time interval T where C is a factor of 180; (7-2) the rotating motor controls the connecting column to drive the two electrodes to rotate counterclockwise by C degrees for each time interval T after a continuous clockwise rotation of 180 degrees, and proceeds to step (7-1) after a continuous counterclockwise rotation of 180 degrees.

7. The control method of the antiemetic control device according to claim 5, further comprising a memory and a wireless transceiver disposed in the housing, wherein the memory and the wireless transceiver are electrically connected to the MCU microcontroller, and the method further comprises the following steps: the MCU microcontroller stores a date, a start time and a stop time of the user's electrical pulse stimulation in the memory, the wireless transceiver sends the date, the start time and the stop time of each process of the electrical pulse stimulation to a hospital's information platform or a doctor's cellphone.

8. The control method of the antiemetic control device according to claim 5, wherein A is 0.5 Hz to 3 Hz, and B is 20 Hz to 35 Hz.

* * * * *